United States Patent
Redmond et al.

(10) Patent No.: US 12,295,678 B2
(45) Date of Patent: May 13, 2025

(54) SYSTEMS AND METHODS FOR INTRAOPERATIVE RE-REGISTRATION

(71) Applicant: Medtronic Navigation, Inc., Louisville, CO (US)

(72) Inventors: Jerald L. Redmond, Germantown, TN (US); Stanley T. Palmatier, Olive Branch, MS (US); Victor D. Snyder, Erie, CO (US); Nikita Pandey, Broomfield, CO (US); Anisha A. Parkar, Thornton, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 341 days.

(21) Appl. No.: 17/589,971

(22) Filed: Feb. 1, 2022

(65) Prior Publication Data

US 2022/0249180 A1     Aug. 11, 2022

Related U.S. Application Data

(60) Provisional application No. 63/147,062, filed on Feb. 8, 2021.

(51) Int. Cl.
    *G06T 7/73*        (2017.01)
    *A61B 34/20*      (2016.01)
    (Continued)

(52) U.S. Cl.
    CPC .............. *A61B 34/30* (2016.02); *A61B 34/20* (2016.02); *G06T 7/337* (2017.01); *G06T 7/74* (2017.01);
(Continued)

(58) Field of Classification Search
CPC . A61B 34/20; A61B 34/30; A61B 2034/2059; G06T 7/73; G06T 7/74;
(Continued)

(56) References Cited

U.S. PATENT DOCUMENTS 7,497,621 B2    3/2009   Yatesenko et al.
7,831,096 B2   11/2010   Williamson, Jr.
(Continued)

FOREIGN PATENT DOCUMENTS

CN      108140242     6/2018
EP        3375400       9/2018
(Continued)

OTHER PUBLICATIONS

International Search Report and Written Opinion for International (PCT) Patent Application No. PCT/US2022/015507, dated Jul. 18, 2022, 18 pages.

(Continued)

*Primary Examiner* — Tuan H Nguyen
(74) *Attorney, Agent, or Firm* — Sheridan Ross P.C.

(57) ABSTRACT

A re-registration method includes receiving a first image depicting a reference frame attached to a patient and oriented in a first pose relative to the patient, the first image obtained by an imaging device mounted to a movable support that has been locked in a selected pose; receiving a second image depicting the reference frame oriented in a second pose relative to the patient, the second image obtained by the imaging device with the movable support locked in the selected pose; and updating a registration between the reference frame and the patient to reflect that the reference frame has been moved from the first pose to the second pose.

20 Claims, 4 Drawing Sheets

(51) Int. Cl.
*A61B 34/30* (2016.01)
*G06T 7/33* (2017.01)
*G06V 40/10* (2022.01)

(52) U.S. Cl.
CPC .... *G06V 40/103* (2022.01); *A61B 2034/2059* (2016.02)

(58) Field of Classification Search
CPC ........... G06T 7/337; G06T 7/33; G06V 40/10; G06V 40/103
See application file for complete search history.

(56) References Cited

U.S. PATENT DOCUMENTS

| | | | |
|---|---|---|---|
| 7,835,784 | B2 | 11/2010 | Mire et al. |
| 8,131,031 | B2 | 3/2012 | Lloyd |
| 8,239,001 | B2 | 8/2012 | Verard et al. |
| 8,657,809 | B2 | 2/2014 | Schoepp |
| 8,694,075 | B2 | 4/2014 | Groszmann et al. |
| 8,900,131 | B2 | 12/2014 | Chopra et al. |
| 9,723,976 | B2 | 8/2017 | Tesar |
| 9,901,407 | B2 | 2/2018 | Breisacher et al. |
| 9,990,725 | B2 | 6/2018 | Jeong et al. |
| 10,016,243 | B2 | 7/2018 | Esterberg |
| 10,463,447 | B2 | 11/2019 | Sela et al. |
| 10,603,118 | B2 | 3/2020 | Srimohanarajah et al. |
| 2011/0158488 | A1 | 6/2011 | Cohen et al. |
| 2017/0020622 | A1 | 1/2017 | Huldin et al. |
| 2017/0336220 | A1 | 11/2017 | Broaddus et al. |
| 2017/0348061 | A1 | 12/2017 | Joshi et al. |
| 2018/0153626 | A1 | 6/2018 | Yang et al. |
| 2019/0066314 | A1 | 2/2019 | Abhari et al. |
| 2019/0183589 | A1 | 6/2019 | Cappadona et al. |
| 2019/0208180 | A1 | 7/2019 | Xiong et al. |
| 2019/0320878 | A1 | 10/2019 | Duindam et al. |

FOREIGN PATENT DOCUMENTS

| | | |
|---|---|---|
| KR | 10-2017-0055393 | 5/2017 |
| WO | WO 2013/192598 | 12/2013 |
| WO | WO 2018/049196 | 3/2018 |

OTHER PUBLICATIONS

Chen et al. "Development of a surgical navigation system based on augmented reality using an optical see-through head-mounted display," Journal of Biomedical Informatics, Jun. 2015, vol. 55, pp. 124-131.

Gundle et al. "Accuracy and Precision of a Surgical Navigation System: Effect of Camera and Patient Tracker Position and Number of Active Markers," The Open Orthopaedics Journal, 2017, vol. 11, (Suppl-3, M4) pp. 493-501.

Manni et al. "Towards Optical Imaging for Spine Tracking without Markers in Navigated Spine Surgery," Sensors, Jul. 2020, vol. 20, No. 13, article 3641, 17 pages.

Suess et al. "Study on the clinical application of pulsed DC magnetic technology for tracking of intraoperative head motion during frameless stereotaxy," Head & Face Medicine, 2006, vol. 2, article No. 10, 19 pages.

Pei-Lun et al., "Surgical Navigation System Based on the Visual Object Tracking Algorithm," 2018 4th Annual International Conference on Network and Information Systems for Computers (ICNISC), Wuhan, China, 2018, pp. 160-164.

SYSTEMS AND METHODS FOR INTRAOPERATIVE RE-REGISTRATION

CROSS REFERENCE TO RELATED APPLICATIONS

This application claims the benefit of U.S. Provisional Application No. 63/147,062, filed on Feb. 8, 2021, and entitled "SYSTEMS AND METHODS FOR INTRAOPERATIVE RE-REGISTRATION," which application is incorporated herein by reference in its entirety.

FIELD

The present technology generally relates to surgical procedures requiring registration between a patient coordinate space and another coordinate space, and relates more particularly to intraoperative re-registration during such procedures.

BACKGROUND

Surgical robots may assist a surgeon or other medical provider in carrying out a surgical procedure, or may complete one or more surgical procedures autonomously. Additionally, one or more navigation systems may be used to track a location of various reference markers attached to surgical tools, anatomical elements, and/or other objects during a surgery. Prior to beginning a given surgical procedure, a registration process may be completed to correlate two or more coordinate spaces with each other, including, for example, coordinate spaces of one or more robots, navigation systems, imaging devices, reference frames, and/or patients.

SUMMARY

Example aspects of the present disclosure include:

A re-registration method comprising: receiving a first image depicting a reference frame attached to a patient and oriented in a first pose relative to the patient, the first image obtained by an imaging device mounted to a movable support that has been locked in a selected pose; receiving a second image depicting the reference frame oriented in a second pose relative to the patient, the second image obtained by the imaging device with the movable support locked in the selected pose; and updating a registration between the reference frame and the patient to reflect that the reference frame has been moved from the first pose to the second pose.

Any of the aspects herein, comprising: receiving an initial registration between a reference frame and a patient, the initial registration based on the reference frame being in the first pose relative to the patient.

Any of the aspects herein, wherein the reference frame is attached to the patient via an adjustable reference frame mount.

Any of the aspects herein, wherein when the reference frame is in the first pose, the adjustable reference frame mount is secured to a vertebra of the patient.

Any of the aspects herein, wherein when the reference frame is in the second pose, the adjustable reference frame mount is still secured to the vertebra of the patient.

Any of the aspects herein, wherein the movable support is a robotic arm.

Any of the aspects herein, wherein the movable support comprises at least one selectively lockable joint.

Any of the aspects herein, wherein the second image is obtained by the imaging device within thirty seconds of the reference frame reaching the second pose.

Any of the aspects herein, wherein the imaging device is a navigation system camera.

Any of the aspects herein, wherein the imaging device is a structured light camera.

Any of the aspects herein, wherein the step of updating the registration comprises calculating a transformation between a new reference frame coordinate space and a patient coordinate space based on a previous registration.

A system for intraoperative re-registration, comprising: a robotic arm; an imaging device mounted to the robotic arm; a processor; and a memory storing instructions for execution by the processor. The instructions, when executed, cause the processor to: cause the imaging device to capture a first image at a first time, the first image depicting a reference frame attached to a patient and oriented in a first pose relative to the patient; cause the imaging device to capture a second image at a second time after the first time, the second image depicting the reference frame attached to the patient and oriented in a second pose relative to the patient, the second pose different than the first pose; and update a registration between the reference frame and the patient to reflect that the reference frame has been moved from the first pose to the second pose.

Any of the aspects herein, wherein the memory stores additional instructions for execution by the processor that, when executed, further cause the processor to: transmit a signal, before the first time and based on a user input, that causes the robotic arm to be locked in a selected pose.

Any of the aspects herein, wherein the selected pose is a predetermined pose different than a pose of the robotic arm when the signal is transmitted.

Any of the aspects herein, wherein the memory stores additional instructions for execution by the processor that, when executed, further cause the processor to: determine a first imaging device pose at the first time; determine a second imaging device pose at the second time; and determine, based on the first image, the first imaging device pose, the second image, and the second imaging device pose, a transformation between the second pose and the first pose.

Any of the aspects herein, wherein the memory stores additional instructions for execution by the processor that, when executed, further cause the processor to: update the registration between the reference frame and the patient, based on the determined transformation, to reflect that the reference frame has been moved from the first pose to the second pose.

Any of the aspects herein, wherein causing the imaging device to capture the first image occurs in response to a user input.

A re-registration system comprising: a reference frame mount fixedly attachable to a patient; a reference frame adjustably attached to the reference frame mount; an inertial measurement unit (IMU) fixedly secured to the reference frame; a communication interface; a processor; and a memory. The memory stores instructions for execution by the processor that, when executed, cause the processor to: receive, via the communication interface, information corresponding to motion detected by the IMU; determine, based on the information, a change in pose of the reference frame; and update an existing registration between the reference frame and the patient based on the determined change in pose.

Any of the aspects herein, wherein the memory stores additional instructions for execution by the processor that, when executed, further cause the processor to: receive a first user input indicating that a pose of the reference frame will be adjusted; and receive a second user input indicating that adjustment of the pose of the reference frame is complete; wherein the information corresponds to motion detected by the IMU between receipt of the first user input and the second user input.

Any of the aspects herein, wherein the IMU is a first IMU, the re-registration system further comprising a second IMU different than the first IMU and fixedly securable relative to an anatomical element of a patient.

Any of the aspects herein, wherein the information is first information, the change in pose of the reference frame is a first change in pose, and the memory stores additional instructions for execution by the processor that, when executed, further cause the processor to: receive, via the communication interface, second information corresponding to motion detected by the second IMU; determine, based on the second information, a change in pose of the anatomical element; and update the existing registration between the reference frame and the patient based on the determined first change in pose and the determined second change in pose.

An intraoperative re-registration system comprising: a reference frame mount fixedly attachable to a patient; a reference frame attached to the reference frame mount and adjustable between a first predetermined pose relative to the reference frame mount and a second predetermined pose relative to the reference frame mount; a processor; and a memory. The memory stores information about the first predetermined pose and the second predetermined pose, and instructions for execution by the processor that, when executed, cause the processor to: receive an input indicating that the reference frame has been moved from the first predetermined pose to the second predetermined pose; and update, in response to the input, an existing registration between the reference frame and the patient based on the information.

Any of the aspects herein, wherein the input is generated automatically.

Any of the aspects herein, wherein the input is provided by a user.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Image-guided surgery of the spine may utilize 3D image data from CT or 3D fluoroscopy to create a virtual map of the patient's anatomy that can be registered to the patient's physical position. This virtual map allows for real-time localization of instruments and implants relative to the patient's anatomy in 3D space, utilizing computer systems equipped with tracking technologies and software. The image data can be acquired several days before the surgery or just prior to the surgery, with both manual and automatic registration techniques available for registering the image data to the patient. A key component of both manual and automatic registration involves use of a patient reference frame, where a tracking instrument or imaging phantom is attached to the patient during collection of image data and its position relative to the position of the imaging system is utilized by the image guidance software to orient and position the image data to the patient's physical position in 3D space.

A limitation of image guidance systems is the inability to account for movement of the reference frame relative to the patient's anatomy after registration. Collection of additional images (e.g., with ionizing radiation) may be needed if the reference frame is moved or bumped out of its initial position relative to the patient's anatomy. The labor-intensive (especially for spinal surgeries) manual registration process may need to be performed or repeated if the reference frame is moved or bumped out of its previous position. Embodiments of the present disclosure allow for intra-procedure repositioning of the reference frame without the need for acquiring new image data or for performing or repeating a complete manual (e.g., touch-based) registration.

According to some embodiments of the present disclosure, a change in pose of the reference frame may be determined and/or communicated to an image guidance system (e.g., a navigation system) using optical-based measurement with a visible light or infrared light camera, or sensor-based measurement with an inertial measurement unit. Embodiments of the present disclosure also include an algorithm for updating an image registration based on a measured change in the reference frame pose, including application of transforms to re-register the image data to the new frame pose; and an algorithm to update a pose of specific anatomical structures after re-registration if necessary (using prior saved locations from a tracked instrument to correct for inaccuracy if anatomy shift occurred between registrations).

Imaged-guided surgery and robotic surgery provide significant enhancements to the accuracy and reproducibility of spine surgical procedures. However, the dependency on a physical reference frame for localization can be disruptive to the procedural workflow, where the size of the frame can interfere with procedural steps and inadvertent bumping of the frame can result in loss of image registration, requiring in some instances additional X-ray exposure to the patient and operating room staff. The ability to update the image registration without the need for additional imaging (e.g., without using ionizing radiation), and/or without the need to perform or repeat a manual registration process that requires valuable time and is therefore expensive, would provide surgeons with the flexibility to reposition the frame during the procedure to accommodate the needs of the procedure and patient anatomy, enhancing efficiency and improving patient satisfaction and outcomes.

Embodiments of the present disclosure provide technical solutions to one or more of the problems of (1) enabling a reference frame to be moved intraoperatively (intentionally or unintentionally) without necessitating a lengthy and expensive re-registration procedure; (2) detecting intentional and/or unintentional movement of a reference frame relative to a patient; (3) intraoperatively updating an existing registration without using ionizing radiation and without performing or repeating a complete manual (e.g., touch-based) registration; and (4) reducing an amount of ionizing radiation to which a patient and/or medical staff are exposed during a surgical procedure.

Figure 1:
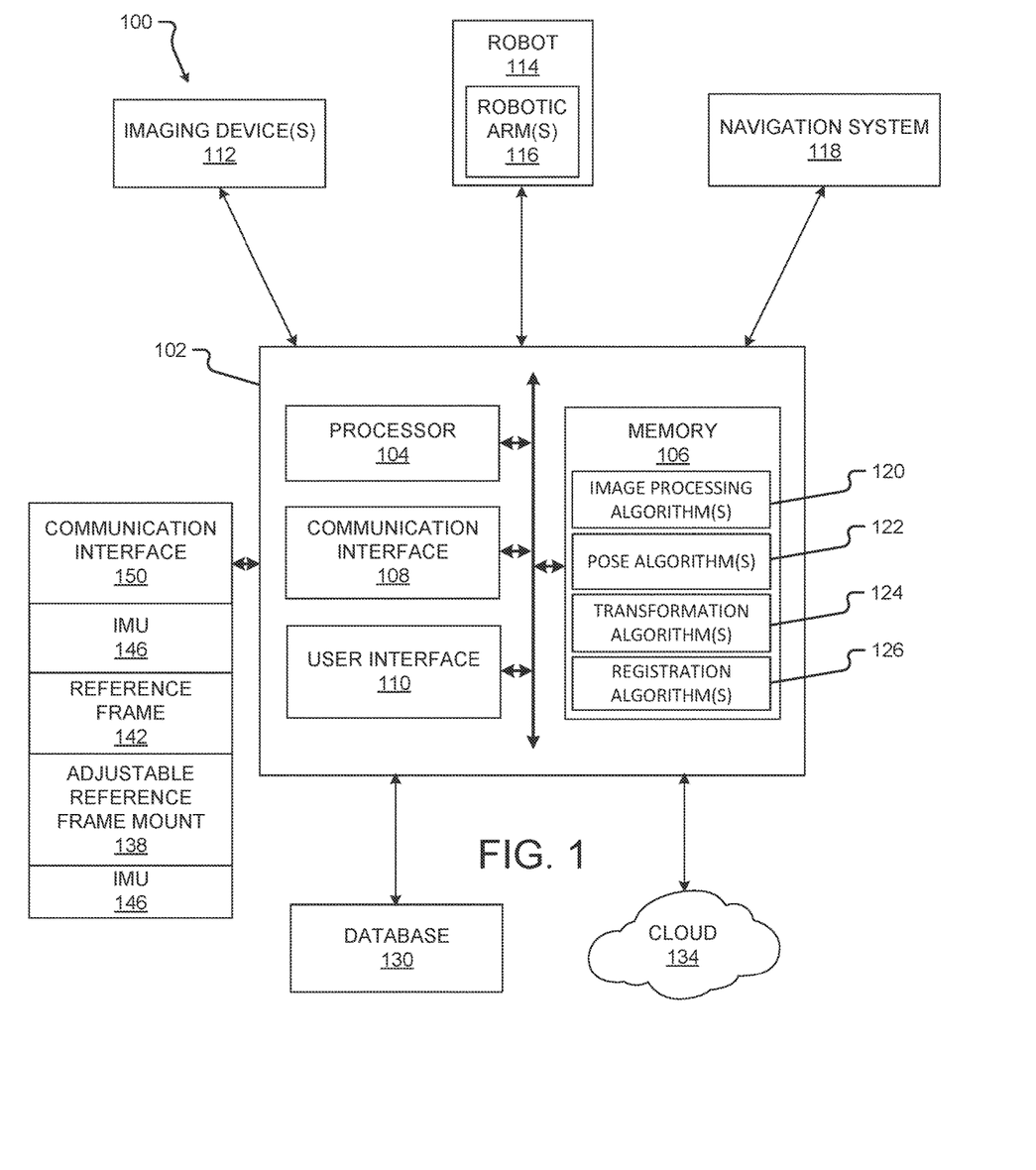
FIG. 1 is a block diagram of a system according to at least one embodiment of the present disclosure.

Turning first to FIG. 1, a block diagram of a system 100 according to at least one embodiment of the present disclosure is shown. The system 100 may be used for intraoperative re-registration of one coordinate space to another (e.g., of a reference frame and/or navigation coordinate space to a patient coordinate space) without exposing a patient to ionizing radiation and without performing or repeating a complete manual (e.g., touch-based) registration, and/or to carry out one or more other aspects of one or more of the methods disclosed herein. The system 100 comprises a computing device 102, one or more imaging devices 112, a robot 114, a navigation system 118, a database 130, a cloud or other network 134, an adjustable reference frame mount 138, a reference frame 142, one or more inertial measurement units (IMUs) 146, and a communication interface 150. Systems according to other embodiments of the present disclosure may comprise more or fewer components than the system 100. For example, the system 100 may not include the imaging device 112, the robot 114, the navigation system 118, one or more components of the computing device 102, the database 130, the cloud 134, the adjustable reference frame mount 138, the reference frame 142, the one or more inertial measurement units (IMUs) 146, and the communication interface 150. Additionally, the system 100 may comprise one or more tools to which a tracker (which may be the same as or similar to the reference frame 142) is fixedly secured, to enable the navigation system 118 to track the one or more tools.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, the cloud 134, and/or one or more IMUs 146.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 200, 300, 400, 500, and/or 600 described herein, or of any other methods. The memory 106 may store, for example, one or more image processing algorithms 120, one or more pose algorithms 122, one or more transformation algorithms 124, and/or one or more registration algorithms 126. Such instructions or algorithms may, in some embodiments, be organized into one or more applications, modules, packages, layers, or engines. The algorithms and/or instructions may cause the processor 104 to manipulate data stored in the memory 106 and/or received from or via the imaging device 112, the robot 114, the database 130, the cloud 134, and/or one or more IMUs 146.

The computing device 102 may also comprise a communication interface 108. The communication interface 108 may be used for receiving image data, movement information, or other data or information from an external source (such as the imaging device 112, the robot 114, the navigation system 118, the database 130, the cloud 134, one or more IMUs 146, and/or any system or component), and/or for transmitting instructions, images, or other information to an external system or device (e.g., another computing device 102, the imaging device 112, the robot 114, the navigation system 118, the database 130, the cloud 134, and/or any other system or component). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), a magnetic resonance imaging (MM) scanner, an optical coherence tomography (OCT) scanner, an endoscope, a microscope, a thermographic camera (e.g., an infrared camera), an optical camera, a structured light camera, a radar system (which may comprise, for example, a transmitter, a receiver, a processor, and one or more antennae), or any other imaging device 112 suitable for obtaining images of a reference marker and/or of an anatomical feature of a patient. When used in connection with an initial registration, but otherwise only when explicitly stated, the imaging device 112 may be an O-arm, a C-arm, a G-arm, or any other device utilizing X-ray-based imaging (e.g., a fluoroscope, a CT scanner, or other X-ray machine). The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor X™ Stealth Edition robotic guidance system. The robot 114 may be configured to position the imaging device 112, a surgical tool, and/or any other object at one or more precise pose(s), position(s), and/or orientation(s), and/or to return the object to the same position(s) and/or orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, a surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (i.e., navigation markers) may be placed on the robot 114 (including, e.g., on the robotic arm 116), the imaging device 112, or any other object in the surgical space. The reference frame 142, for example, is a reference marker adapted to be secured to an anatomical element of a patient via a mount such as an adjustable reference frame mount 138. The reference frame 142 and any other reference markers may be tracked by the navigation system 118, and the results of the tracking may be used by the robot 114 and/or by an operator of the system 100 or any component thereof. In some embodiments, the navigation system 118 can be used to track other components of the system (e.g., the imaging device 112) and the system can operate without the use of the robot 114 (e.g., with the surgeon manually manipulating the imaging device 112 and/or one or more surgical tools, based on information and/or instructions generated by the navigation system 118, for example).

Reference markers according to embodiments of the present disclosure, including the reference frame 142, may comprise one or more reflective spheres, light emitting diodes (LEDs), infrared emitting diodes (IREDs), and/or other elements detectable by a camera or other sensor(s) of the navigation system 118. Such detectable elements, which may be active (such as LEDs or IREDs) or passive (such as reflective spheres) may each be disposed on a separate arm, corner, and/or other feature of a given reference marker. Each reference marker used in a particular surgery may, in some embodiments, comprise a unique arrangement of detectable elements thereon, so as to enable the navigation system 118 to distinguish one reference marker from another.

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system 118 may comprise one or more electromagnetic sensors. In various embodiments, the navigation system 118 may be used to track a position and orientation (i.e., pose) of the imaging device 112, the robot 114 and/or robotic arm 116, a reference frame 142, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The adjustable reference frame mount 138 may be any device capable of being fixedly secured to an anatomical element of a patient and of supporting a reference frame (e.g., the reference frame 142) in a selected pose relative to the anatomical element. The adjustable reference frame mount 138 may, for example, comprise a pin, screw, clamp, grip, or other gripping or fastening mechanism useful for fixedly securing the mount 138 to an anatomical element (e.g., a vertebra or portion thereof, or a pelvis). The adjustable reference frame mount 138 may be adjustable in one or more dimensions such that the mount 138 is capable of holding the reference frame 142 in a plurality of poses relative to the anatomical element of the patient. In some embodiments, the adjustable reference frame 142 may be configured to hold the reference frame mount in only a limited number (e.g., 1, 2, 3, 4, 5, 6, 7, 8, 9, or 10) of specific poses. In other embodiments, the adjustable reference frame 142 may be configured to hold the reference frame in an any desired pose in one or more degrees of freedom.

The inertial measurement unit(s) 146 may be any IMUs useful for detecting movement of an object. The IMUs 146 may be or comprise a micro-electro-mechanical system (made, for example, of silicon or quartz); a fiber-optic, ring laser, or other type of gyroscope; one or more accelerometers; an attitude and heading reference system (AHRS); and/or any other type of IMU or component thereof. The particular type of IMU(s) 146 used in the system 100 may be selected based on an error tolerance thereof, to ensure that any such error is sufficiently small so as not to negatively affect any position determinations referenced herein to a clinically meaningful extent. The IMUs 146 may be powered, for example, by an internal battery, an external power supply, or any other suitable means. To yield improved resolution in data sensed or otherwise collected by an IMU, any IMU 146 utilized herein may be mounted to an object at a point on the object that is distant from a center of rotation of the object.

Embodiments of the present disclosure that utilize one or more IMUs may alternatively use an electromagnetic navigation or tracking system that comprises, for example, a magnetic field generator and one or more magnetic field sensors attached to any object the pose of which needs to be tracked or determined. In other words, any IMU described herein may be replaced with a magnetic field sensor or other electromagnetic sensor that can detect a generated magnetic field (or other electromagnetic energy) and enable a pose and/or movement determination based on the detected data. In some embodiments, the coordinate systems of the IMU or other sensor and the object to which the IMU or other sensor is mounted may be correlated to each other by calibration during manufacture or otherwise.

The inertial measurement unit(s) 146 may be configured to transmit data generated thereby via a communication interface 150. The communication interface 150 may be wired and/or wireless, and may be configured to transmit data to, for example, the communication interface 108. The communication interface 150 may be identical or substantially similar to the communication interface 108.

The system 100 or similar systems may be used, for example, to carry out one or more aspects of any of the methods 200, 300, 400, 500, and/or 600 described herein. The system 100 or similar systems may also be used for other purposes.

Figure 2:
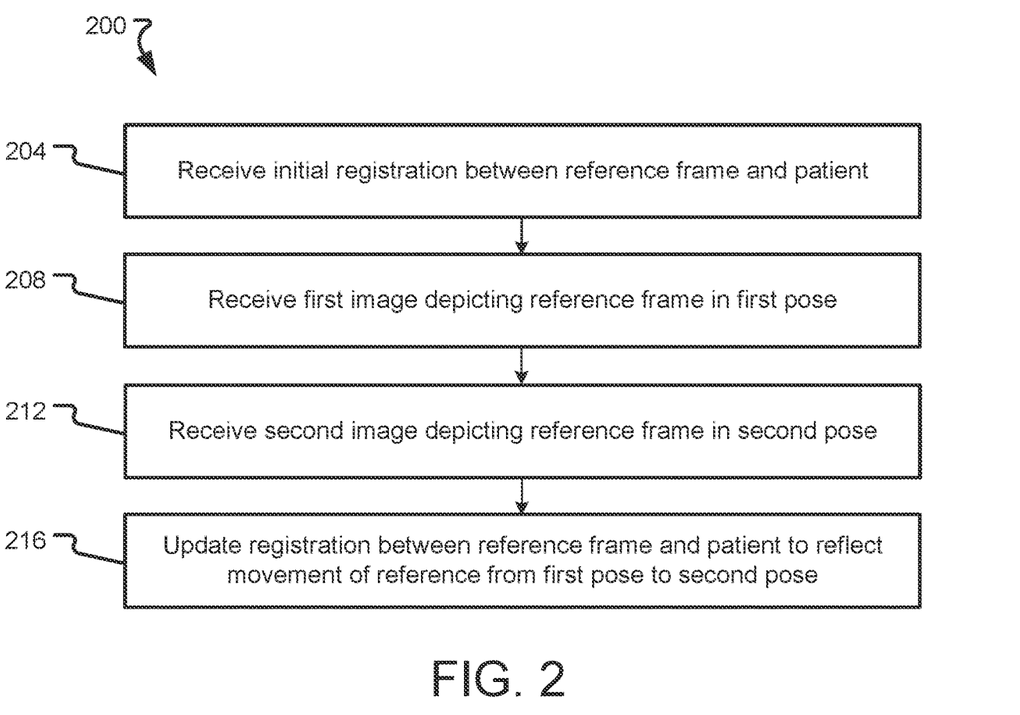
FIG. 2 is a flowchart according to at least one embodiment of the present disclosure.

FIG. 2 depicts a method 200 that may be used, for example, to update an existing registration intraoperatively. The method 200 may be used alone and/or in combination with any other method (or aspect thereof) described herein.

The method 200 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 200. The at least one processor may perform the method 200 by executing instructions stored in a memory such as the memory 106. The instructions may correspond to one or more steps of the method 200 described below. The instructions may cause the processor to execute one or more algorithms, such as an image processing algorithm 120, a pose algorithm 122, a transformation algorithm 124, and/or a registration algorithm 126.

The method 200 comprises receiving an initial registration between a reference frame and a patient (step 204). The initial registration comprises a registration between a navigation coordinate space and a patient coordinate space, although the initial registration may also comprise a registration between a navigation coordinate space and a robotic coordinate space, between a robotic coordinate space and a patient coordinate space, and/or between an imaging device coordinate space and one or more of a robotic coordinate space, a patient coordinate space, and/or a navigation coordinate space. The initial registration may comprise a mapping, transformation, or other correlation or correlating algorithm that enables coordinates defining a particular location with respect to one coordinate space to be converted into coordinates defining the particular location with respect to another coordinate space.

The initial registration may be a registration that was accomplished using, or that is otherwise based on, a reference frame attached to a patient, or more specifically to an anatomical element of the patient. The reference frame may be, for example, a reference frame 142. The reference frame may be secured to the patient in a particular pose, and the accuracy of the registration may depend upon the reference frame remaining in the particular pose relative to the patient.

The initial registration may be a registration that was conducted immediately prior to or at the beginning of a surgical procedure, or a registration that was conducted at any time prior to receipt thereof. The initial registration may be received, for example, from a memory such as the memory 106, from a database such as the database 130, from or via a network such as the cloud 134, from a navigation system such as the navigation system 118, from a robot such as the robot 114, and/or via a communication interface 108.

The method 200 also comprises receiving a first image depicting a reference frame in a first pose relative to a patient (step 208). The reference frame may be, for example, a reference frame 142, and may be mounted to a patient (or, more specifically, to an anatomical element of a patient) via a reference frame mount. In some embodiments, the reference frame mount may be an adjustable reference frame mount such as the adjustable reference frame mount 138. The reference frame may be secured to the patient via the reference frame mount in a first pose that corresponds to the initial registration. In other words, the initial registration may have been completed based on the reference frame being in the first pose, and may be valid only for as long as the reference frame is in the first pose. Thus, if the reference frame is moved out of the first pose, whether intentionally or unintentionally, the initial registration may no longer be usable for guidance or otherwise during the surgical procedure, and re-registration may be required.

The first image may be obtained using an imaging device such as the imaging device 112, which may be mounted to a movable, but selectively lockable, support. For example, the movable support may comprise a frame with two or more segments connected by one or more joints, so as to provide one or more degrees of freedom of movement to facilitate positioning of the imaging device in a useful position for any given surgical task. Each of the joints may, however, be lockable, so that when the imaging device needs to remain in a fixed position—such as during a re-registration process pursuant to the method 200—the movable frame can be selectively locked in its then-current pose, thus preventing the imaging device from moving. In some embodiments, the movable support may comprise, for example, a robotic arm such as the robotic arm 116 of the robot 114. In such embodiments, the robotic arm may likewise be selectively lockable, such that once the robotic arm has been maneuvered to place the imaging device in a desired pose, the robotic arm may be locked in place to prevent inadvertent movement thereof. The robotic arm may be locked in position by one or more of a mechanical lock, an electronic lock, a magnetic lock, or any other known locking mechanism or device.

The imaging device may be an optical imaging device, an infrared imaging device, a structured light imaging device, or any other imaging device that does not use ionizing radiation. Where a structured light imaging device is used, the imaging device may project a light pattern onto, for example, the patient anatomy; detect one or more features in the image; and use the projected light pattern to align the detected features with a model or another image.

The method 200 also comprises receiving a second image depicting a reference frame in a second pose relative to the patient. The second image is obtained using the same imaging device, in the same pose, as the first image. In other words, the imaging device use to capture the first image is also used to capture the second image, and when capturing the second image the imaging device is in the same position and orientation as when capturing the first image. As a result, any movement of the reference frame or any other object in the image reflects movement of the reference frame or other object itself, as opposed to movement of the imaging device used to capture the second image.

The reference frame as depicted in the second image is in a second pose different than the first pose. The second pose may be, for example, a pose that allows a surgeon, a surgical robot, or any other person or tool better access to a surgical site. In other words, the second pose may be a pose in which the reference frame does not present a physical obstacle to completion of a particular surgical task or procedure.

Thus, for example, if a particular surgical procedure requires that pedicle screws be implanted in five different vertebrae along a patient's spine, the reference frame may be affixed (whether directly or via a reference frame mount) to a vertebra that lies between any two of the five vertebrae in which pedicle screws are to be implanted. The reference frame may initially be oriented (e.g., for purposes of an initial registration) in a first pose that allows drilling/tapping/screw implantation access to some of the vertebrae in question but blocks access to others of the vertebrae in question. Once pedicle screws have been implanted in the first subset of vertebrae, however, the reference frame may need to be moved from the first pose to a second pose that allows access to the remaining vertebrae in question, while blocking access to one or more of the vertebrae in which one or more pedicle screws have already been implanted. In this example, the first image (of the step 208) would be obtained prior to moving the reference frame from the first pose to the second pose, and the second image (of the present step 212) would be obtained after moving the reference frame from the first pose to the second pose.

In some embodiments, the second pose may reflect a simple rotation of the reference frame around an axis, or a simple translation of the reference frame along a linear path. In other embodiments, the second pose may be a more substantial repositioning and/or reorientation of the reference frame, but without any change in a point of attachment of the reference frame to the patient (whether the attachment is direct or via a reference frame mount). In still other embodiments, the second pose may involve detaching the reference frame (and/or the reference frame mount, if used) from a first anatomical element of the patient, and reattaching the reference frame (and/or the reference frame mount) either to a different position on the first anatomical element or to a second anatomical element different than the first anatomical element.

The method 200 also comprises updating the initial registration (or another registration) between the reference frame and the patient to reflect movement of the reference frame from the first pose to the second pose (step 216). The updating may comprise, for example, detecting the reference frame in the second pose, as depicted in the second image, determining an offset between the first pose and the second pose, calculating a transformation from the first pose to the second pose or vice versa, and/or using the initial registration together with the calculated transformation to generate an updated registration. Any one or more aspects of an updating a registration as described in connection with any other method disclosed herein may also be used in connection with the step 216, and vice versa. The step 216 may utilize one or more of an image processing algorithm 120, a pose algorithm 122, a transformation algorithm 124, and/or a registration algorithm 126.

Where the initial registration is a registration between a navigation, reference frame, or other image guidance system coordinate space and a patient coordinate space, the updating the registration may comprise identifying a transformation, mapping, or other correlation between the first pose and the second pose, which may then be used together with the initial registration to translate one or more coordinates in the patient coordinate space to one or more coordinates in the image guidance system coordinate space and/or vice versa. In such embodiments, the translation process using the updated registration may comprise two steps: a first step that involves translating the one or more coordinates from the patient coordinate space to the image guidance system coordinate space (or vice versa) using the initial registration (which is no longer accurate); and a second step that involves translating the inaccurate results of the first step into accurate coordinates using the identified transformation, mapping, or other correlation.

In other embodiments, updating the registration may comprise utilizing an identified transformation, mapping, or other correlation between the first pose and the second pose, together with the initial registration, to determine a new, direct transformation from one coordinate space directly to the other coordinate space that no longer requires use of the initial registration.

In still other embodiments, updating the registration may comprise utilizing a navigated pointer tool (e.g., a metal rod having a reference frame such as the reference frame 142, or any other reference marker trackable by the navigation system 118, on a proximal end thereof) to touch a plurality of points (e.g., with a distal end of the pointer tool) on one or more anatomical elements of the patient. The touched points may be, for example, points whose precise position relative to the reference frame in its first pose was known (whether due to using the navigated pointer tool for purposes of the initial registration, or in preparation for the method 200, or otherwise). While some touch-based registration processes require that the touched points be clearly identifiable in a CT scan, in at least some embodiments of the present disclosure, the touched points may be identified in space using the navigated pointer tool and not identifiable in a CT scan or other imagery or model. In other words, the present disclosure encompasses the use of touched points that are not identifiable in a CT scan or other imagery or model. By using the navigated pointer tool to touch the points in question after the reference frame 142 has been moved to the second pose, a new position of the patient relative to the reference frame 142 in the second pose may be determined, and used to update the initial registration. This may be particularly useful where the patient's pose in the second image is different than the patient's pose in the first image (or if there is any other reason to believe that the patient has moved). In such embodiments, the updated registration may be used independently of the initial registration, as a direct correlation may be established between the coordinate system of the reference frame in the second pose and the patient coordinate system.

Regardless of precisely how the updated registration is obtained or effected, that registration may be used for as long as the spatial relationship between the patient and the reference frame remains fixed. In other words, provided the frame remains in the second pose relative to the patient, the updated registration may be used to provide navigation or other image-based guidance in connection with a surgical procedure on the patient.

The present disclosure encompasses embodiments of the method 200 that comprise more or fewer steps than those described above, and/or one or more steps that are different than the steps described above.

Figure 3:
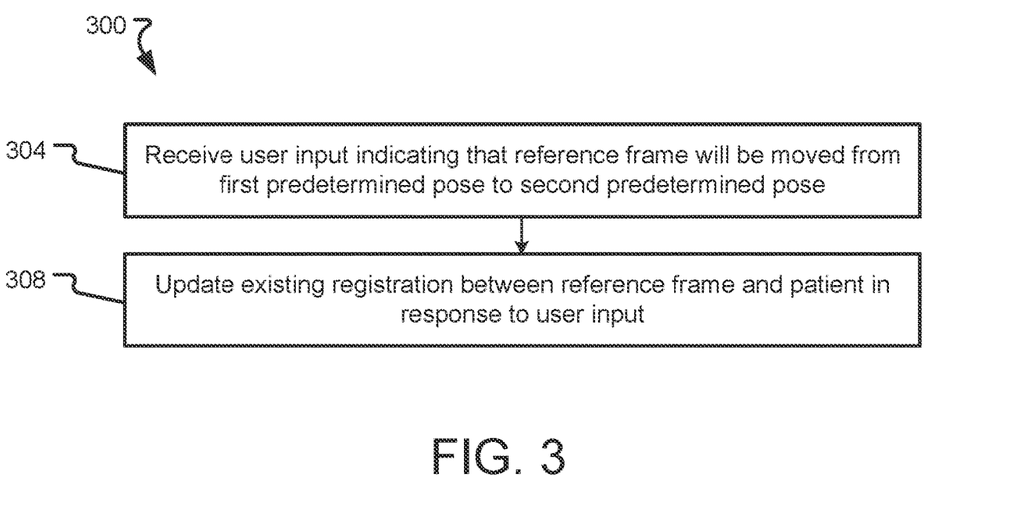
FIG. 3 is a flowchart according to at least one embodiment of the present disclosure.

FIG. 3 depicts a method 300 that may be used, for example, to update an existing registration intraoperatively. The method 300 may be used alone and/or in combination with any other method (or aspect thereof) described herein.

The method 300 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 300. The at least one processor may perform the method 300 by executing instructions stored in a memory such as the memory 106. The instructions may correspond to one or more steps of the method 300 described below. The instructions may cause the processor to execute one or more algorithms, such as an image processing algorithm 120, a pose algorithm 122, a transformation algorithm 124, and/or a registration algorithm 126.

The method 300 comprises receiving user input indicating that a reference frame will be moved from a first predetermined pose to a second predetermined pose (step 304). The first predetermined pose may be, for example, one of a limited number of possible poses of a reference frame relative to a reference frame mount. Moreover, information about each one of the limited number of possible poses of the reference frame relative to the reference frame mount may be stored in a memory (e.g. a memory 106 and/or a database 130) and/or otherwise accessible to a processor executing the method 300. The information may be or include information about an angle of each one of the limited number of possible poses relative to another one or more possible poses and/or relative to a reference angle, and may be used to enable a processor to calculate a pose of each element of the reference frame relative to the other one or more possible poses and/or relative to the reference angle.

Alternatively, information about a pose of each element of the reference frame and/or a pose of the reference frame as a whole when the reference frame is in each of the limited number of possible poses may be stored in a memory and/or otherwise accessible to the processor executing the method 300. The information may be calculated information (calculated, e.g., based on information about the reference frame and information about each of the limited number of possible poses) or measured information (measured, e.g., by placing the reference frame in each of the limited number of possible poses and taking any needed measurements).

The user input may be received, for example, via a user interface such as the user interface 110. In some embodiments, the user input may comprise a first input indicating that the reference frame is going to be moved from an existing pose to a new pose, and a second input indicating that the movement has been completed. In such embodiments, the first user input may specify one of the limited number of possible poses that the reference frame currently occupies, and/or one of the limited number of possible poses to which the reference frame will be moved. Additionally or alternatively, the second user input may indicate one of the limited number of possible poses from which the reference frame was moved, and/or the one of the limited number of possible poses to which the reference frame was moved. In some embodiments, however, the previous and/or a new predetermined pose of the reference frame may be determined using imagery (e.g., by comparing one or more images of the reference frame in its previous pose and/or in its new pose to known information about the limited number of possible poses).

Although the step 304 is described as receiving a user input indicating that a reference frame will be moved from a first predetermined pose to a second predetermined pose, in some embodiments of the present disclosure, the step 304 may alternatively comprise receiving an automatically generated input indicating that a reference frame will be moved (or is being moved, or has moved) from a first predetermined pose to a second predetermined pose. In such embodiments, the input may be generated automatically by, for example, one or more sensors tracking a pose of the reference frame relative to a pose of the patient (or vice versa).

The method 300 also comprises updating an existing registration between the reference frame and the patient in response to the user input (step 308). The step 308 may be the same as or similar to the step 216 of the method 200 (and/or may utilize any aspect thereof). The existing registration may be the same as or similar to the initial registration described above. The updating may comprise, for example, accessing information regarding the previous and/or the new predetermined pose, which information may be stored in a memory such as the memory 106, a navigation system such as the navigation system 118, a database such as the database 130, and/or a network such as the cloud 134. Because each of the possible predetermined poses of the reference frame are known, one or more images of the reference frame in its new pose may not be needed. Instead, the existing registration information (which correlates the reference frame in its previous pose to the patient based on the reference frame being secured to a particular anatomical element of the patient) may be used together with information about the new (predetermined) pose of the reference frame to generate the updated registration.

If, however, the reference frame is moved to a different anatomical element of the patient (as opposed to simply being moved from a first predetermined pose relative to a reference frame mount to a second predetermined pose relative to a reference frame mount), and the attachment to the different anatomical element does not correspond to a known, predetermined pose of the reference frame, then one or more images may be required to properly correlate the reference frame to the patient based on the reference's frame new point of attachment to the patient.

The registration is updated in the step 308 in response to the user input received in the step 304. This ensures that the registration is only updated after the reference frame has been moved from the first predetermined pose to the second predetermined pose. Although the method 300 is described in connection with a user input, in some embodiments, one or more sensors (e.g., a position sensor configured to detect a position and/or orientation of the reference frame relative to a reference frame mount) may be configured to automatically generate a signal (which may be received as an input by a processor executing the method 300) when a change in position and/or orientation of the reference frame is detected. Any other automated or semi-automated means for triggering an update to an existing registration when a change in pose of a reference frame has occurred is encompassed within the scope of the present disclosure.

The present disclosure encompasses embodiments of the method 300 that comprise more or fewer steps than those described above, and/or one or more steps that are different than the steps described above.

Figure 4:
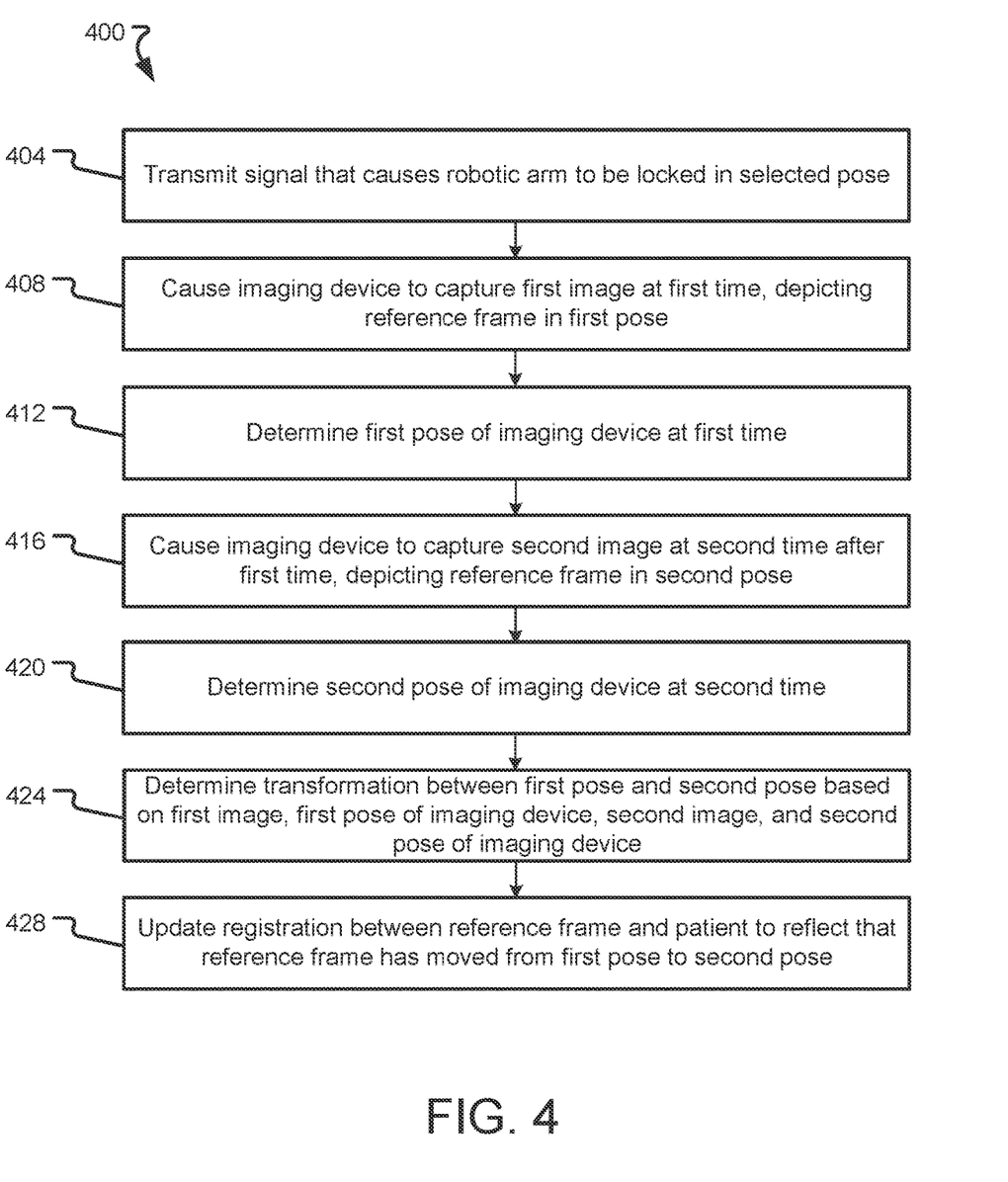
FIG. 4 is a flowchart according to at least one embodiment of the present disclosure.

FIG. 4 depicts a method 400 that may be used, for example, to update an existing registration intraoperatively. The method 400 may be used alone and/or in combination with any other method (or aspect thereof) described herein.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 400. The at least one processor may perform the method 400 by executing instructions stored in a memory such as the memory 106. The instructions may correspond to one or more steps of the method 400 described below. The instructions may cause the processor to execute one or more algorithms, such as an image processing algorithm 120, a pose algorithm 122, a transformation algorithm 124, and/or a registration algorithm 126.

The method 400 comprises transmitting a signal that causes a robotic arm to be locked in a selected pose (step 404). The signal may be sent in response to a user input. For example, if a surgeon or other user wishes to reorient a reference frame used for an initial registration, whether to gain access to a portion of a patient's anatomy that is currently blocked by the reference frame or otherwise, then the user may provide an input (via, for example, a user interface such as the user interface 110) to that effect. In some embodiments, the signal may be sent based on a surgical plan. For example, for an autonomous robotic surgery, or even for a surgery that involves image guidance using a navigation system, progress through a surgical plan may be automatically tracked, and the surgical plan may identify a particular point in a surgical procedure when a reference frame needs to be reoriented relative to a patient. When that particular point is reached, the signal causing a robotic arm to be locked in a selected pose may be transmitted.

The robotic arm locked in the selected pose may be a robotic arm 116 or any other robotic arm. The robotic arm supports an imaging device that will be used to capture images during re-registration pursuant to the method 400. The imaging device may be held at a distal end of the robotic arm (e.g., an end of the robotic arm closest to a patient and farthest from a robot base supporting the robotic arm), or anywhere else along the robotic arm.

The selected pose is a pose from which a field of view of the imaging device includes a reference frame secured to a patient (or, more specifically, to an anatomical element of a patient) as well as at least a portion of the patient. The selected pose may be any one of a number of possible poses, provided that the imaging device remains in the selected pose for at least the steps 408 and 416 described below.

The robotic arm may be locked in the selected pose in response to the transmitted signal (e.g., upon receipt of the transmitted signal) by one or more mechanical locks, electromechanical locks, pneumatic locks, hydraulic locks, magnetic locks, or any other type of lock. In some embodiments, the locking may comprise turning off or otherwise removing power from one or more actuators, servos, or other devices used to move the robotic arm, so that the robotic arm cannot be unintentionally moved from the selected pose. In other embodiments, the step 404 comprises transmitting a signal that causes a robotic arm to actively use one or more actuators, servos, or other devices so as to move the robotic arm to a selected pose and/or to keep the robotic arm in the selected pose despite one or more forces that may be exerted thereon.

Locking the robotic arm in the selected pose may, in some embodiments, comprise not just locking the one or more joints of the robotic arm in a particular pose to keep the robotic arm in the selected pose, but also locking the robotic base in place—whether by using any locking mechanism or device described herein to lock the robotic base to a frame supporting the robotic base, and/or to lock one or more wheels supporting the robotic base so that the robotic base cannot roll or be rolled to a different position, or otherwise.

In some embodiments, the step 404 may be omitted from the method 400.

The method 400 also comprises causing an imaging device to capture a first image at a first time, depicting a reference frame in a first pose (step 408). The first image may be the same as or similar to the first image described above in connection with the step 208 of the method 200. The imaging device may be an imaging device described herein that does not emit ionizing radiation. The causing may comprise transmitting a signal to the imaging device that triggers a shutter of the imaging device. The causing may occur in response to a user input, or automatically based on a particular point of a surgical plan being reached, the robotic arm being locked in the selected pose, or any other predetermined triggering event. The first time is a time during which the reference frame is in the first pose. In some embodiments, the first pose is a pose that corresponds to an initial or existing registration that involved the reference frame. For example, the first time may be a time immediately after an initial or existing registration is completed (in which case the first image may be used, for example, if the reference frame is inadvertently bumped or otherwise moved during a surgical procedure, thus necessitating re-registration). As another example, the first time may be a time immediately or shortly before the reference frame is intentionally moved.

The method 400 also comprises determining a first pose of the imaging device at the first time (step 412). The determining may be unnecessary when the robotic arm is locked in a selected pose at the first time (e.g., due to completion of the step 404), if the selected pose is known and/or is the same pose from which the imaging device captures the second image described in connection with the step 416 below. The determining may comprise receiving information about a pose of the robotic arm and/or about a pose of the imaging device relative to the robotic arm, and using that information to determine a first pose of the imaging device relative to a coordinate space of interest (e.g., a patient coordinate space or an image-guidance coordinate space). The pose information about the pose of the robotic arm and/or about the pose of the imaging device relative to the robotic arm may be received from one or more of the robotic arm (e.g., from one or more sensors on the robotic arm), from a robot that comprises the robotic arm (e.g., from a controller of the robot), from a navigation system such as the navigation system 118 (which may utilize reference markers on the robotic arm and/or on the imaging device to track a respective pose thereof), from a memory such as the memory 106, from a database such as the database 130, and/or from a network such as the cloud 134. In some embodiments, the determining may comprise simply receiving pose information about a tracked pose of the imaging device from a navigation system, without regarding for a pose of the robotic arm. In still other embodiments, the first pose of the imaging device may be provided by the robotic arm (or the corresponding robot), without the need for any calculations or other determinations involving a pose of the robotic arm.

In some embodiments, particularly when the imaging device is not held by a robotic arm, determining the pose of the imaging device at the first time may comprise receiving information from an IMU attached to the imaging device, which information may either specify a pose of the imaging device or be useful for calculating a pose of the imaging device (based, for example, on a previously known position of the imaging device). An IMU attached to the imaging device may be used in any embodiment of the present disclosure, and may be useful for confirming that the imaging device has not moved from the time of capturing the first image to the time of capturing the second image, and/or for determining a pose of the imaging device at a particular time.

The method 400 also comprises causing the imaging device to capture a second image at a second time after the first time, depicting the reference frame in a second pose (step 416). The step 416 may be the same as or similar to the step 408, except that the second image is captured at the second time instead of the first time, and the reference frame is in the second pose instead of the first pose. Thus, in between the first time and the second time, the reference frame is moved from the first pose to the second pose. Movement of the reference frame from the first pose to the second pose may occur automatically (e.g., using one or more actuators, servos, or other devices on the reference frame and/or on the reference frame mount; using a robotic arm to move the reference frame; or otherwise), manually (e.g., by a surgeon or other user physically moving the reference frame), or with robotic assistance (e.g., using a robotic arm controlled by a surgeon or other user).

The second time may, but need not, immediately follow movement of the reference frame to the second pose.

The method 400 also comprises determining a second pose of the imaging device at the second time (step 420). The step 420 mirrors the step 412.

The steps 412 and 420 may be used when, for example, instead of fixing the imaging device in a particular pose for both the first image captured in the step 408 and the second image captured in the step 416, the imaging device is allowed to or is caused to move in between capture of the first image and the second image. In such embodiments, provided that a pose of the imaging device at the first time and at the second time, respectively, is known or can be determined, the known pose of the imaging device at the first and second times can be used to account for the changed position of the imaging device when the two images were taken, and to determine a change in pose of the reference frame depicted in the first and second images.

The method 400 also comprises determining a transformation between the first pose and the second pose based on the first image, the first pose of the imaging device, the second image, and the second pose of the imaging device (step 424). Where the robotic arm is locked in the selected pose at the first time and the second time, the determining may be based on solely on the first image and the second image, and more specifically on the poses of the reference frame as depicted in the first and second images. The step 424 may utilize one or more algorithms, such as a transformation algorithm 124, to determine the transformation. The transformation may enable a point identified with respect to the reference frame in the first pose to be identified with respect to the reference frame in the second pose. In other words, the transformation may be or comprise a mapping or other correlation between the first pose and the second pose.

The method 400 also comprises updating a registration between the reference frame and the patient to reflect that the reference frame has moved from the first pose to the second pose (step 428). The registration may be an initial or existing registration completed while the reference frame was in the first pose, and may be updated such that a given position relative to a patient may be accurately determined based on a detected position of the reference marker (e.g., using a navigation system 118 or other image guidance system), given that the relative pose of the reference marker to the patient has changed. The updating may be based on the transformation determined in the step 424. The updating may yield an updated registration that utilizes a two-step process to identify accurate coordinates. For example, the updated registration may use the initial registration to determine an initial (inaccurate) set of coordinates relative to the patient, and then use the determined transformation to convert the initial (inaccurate) set of coordinates to a final, accurate set of coordinates relative to the patient. Alternatively, the updating may yield an updated registration useful for directly obtaining a final, accurate set of coordinates relative to the patient, without continued reliance on the initial registration.

The present disclosure encompasses embodiments of the method 400 that comprise more or fewer steps than those described above, and/or one or more steps that are different than the steps described above.

Figure 5:
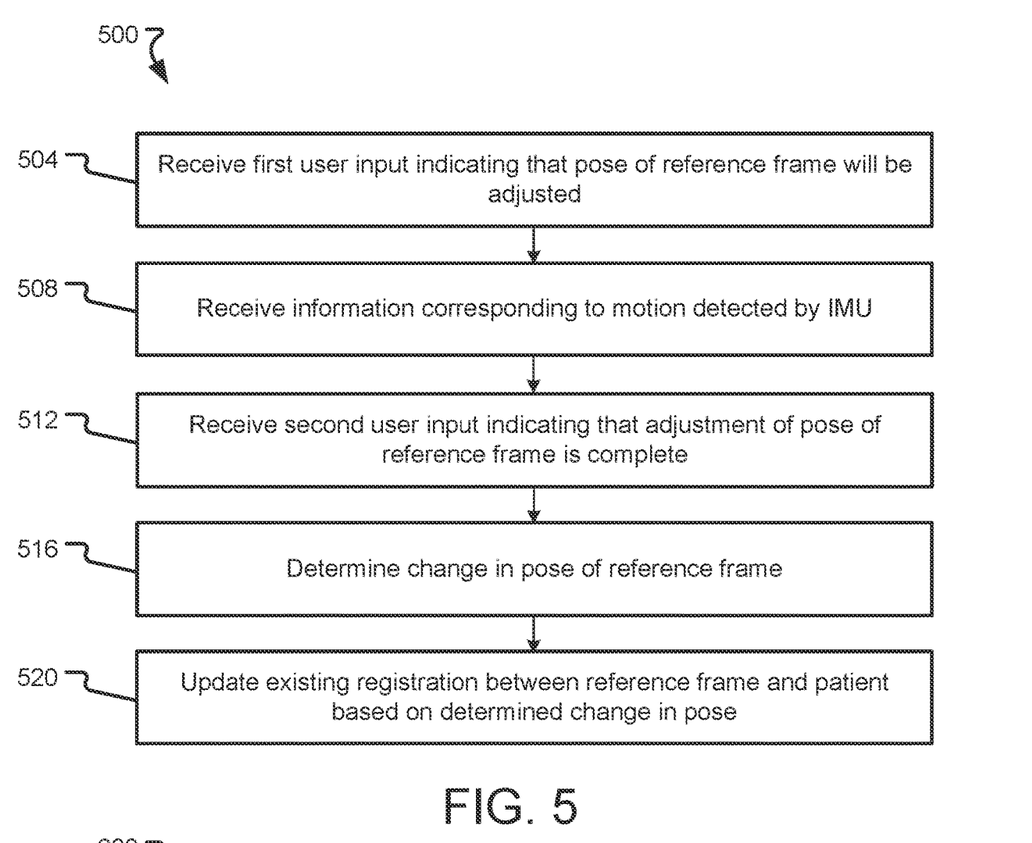
FIG. 5 is a flowchart according to at least one embodiment of the present disclosure.

FIG. 5 depicts a method 500 that may be used, for example, to update an existing registration intraoperatively. The method 500 may be used alone and/or in combination with any other method (or aspect thereof) described herein.

The method 500 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 500. The at least one processor may perform the method 500 by executing instructions stored in a memory such as the memory 106. The instructions may correspond to one or more steps of the method 500 described below. The instructions may cause the processor to execute one or more algorithms, such as an image processing algorithm 120, a pose algorithm 122, a transformation algorithm 124, and/or a registration algorithm 126.

The method 500 comprises receiving a first user input indicating that a pose of a reference frame will be adjusted (step 504). The reference frame may be, for example, a reference frame 142, and may be secured to a patient via a reference frame mount such as the reference frame mount 138, which may in turn be fixedly secured to an anatomical element of the patient. The first user input may be provided via a user interface such as the user interface 110. Prior to receipt of the first user input, any detected motion of the reference frame may be understood and/or treated as reflecting movement of the patient. However, after receipt of the first user input (and prior to a second user input), any detected motion of the reference frame may be understood and/or treated as motion of the reference frame independent of any patient movement.

In some embodiments, instead of receiving a user input indicating that a pose of a reference frame will be adjusted, a determination may be made that a pose of the reference frame will be adjusted. The determination may be based, for example, on a surgical plan. For example, for an autonomous robotic surgery, or even for a surgery that involves image guidance using a navigation system, progress through a surgical plan may be automatically tracked, and the surgical plan may identify a particular point in a surgical procedure when a reference frame needs to be reoriented relative to a patient. When that particular point is reached, the determination that the pose of the reference frame will be adjusted may be made.

The method 500 also comprises receiving information corresponding to motion detected by an IMU (step 508). The IMU may be an IMU 146 or any other IMU, and may be secured to a reference frame such as a reference frame 142. The information may be received via, for example, one or more communication interfaces such as the communication interfaces 108 and/or 150. Thus, the information may received wirelessly or via a wired connection. The information may identify a new pose of the reference frame, and/or may be useful for calculating or otherwise determining a new pose of the reference frame (based, for example, on known information about a previous pose of the reference frame, or a pose of the reference frame when the first user input was received).

The method 500 also comprises receiving a second user input indicating that adjustment of the pose of the reference frame is complete (step 512). Like the first user input, the second user input may be provided via a user interface such as the user interface 110. The second user input provides an indication that any further detected movement of the reference frame corresponds to movement of the patient, to which the reference frame is again fixedly attached.

Here also, in some embodiments, instead of receiving the second user input, a determination may be made that adjustment of a pose of the reference frame is complete. The determination may be based, for example, on the passage of a period of time (e.g., 1 second, 2 seconds, 3 seconds, 4 seconds, 5 seconds, 10 seconds) without any detected movement of the reference frame (e.g., without receiving any indication of movement of the reference frame from the IMU attached thereto).

The method 500 also comprises determining a change in pose of the reference frame (step 516). The change in pose may be determined, for example, based on the information received in the step 508 and corresponding to motion detected by the IMU. An algorithm such as the pose algorithm 122 may be used to determine the change in pose. Where the information provides the new pose of the reference frame without the need for any calculation or other determination thereof, the step 516 may be unnecessary.

The method 500 also comprises updating an existing registration between the reference frame and a patient based on the determined change in pose (step 520). The step 520 may be the same as or similar to, or comprise a combination of one or more aspects of, the step 216 of the method 200, the step 308 of the method 300, and/or the step 428 of the method 400. The existing registration may be a registration completed prior to receipt of the first user input, and based on a previous pose of the reference frame. The updated registration reflects the pose of the reference frame following receipt of the second user input. In some embodiments, the updated registration may utilize a two-step process to identify accurate coordinates relative to the patient based on a known position relative to the reference frame. For example, the updated registration may use the initial registration to determine an initial (inaccurate) set of coordinates relative to the patient, and then use the determined change in pose of the reference frame relative to the patient to convert the initial (inaccurate) set of coordinates to a final, accurate set of coordinates relative to the patient. Alternatively, the updated registration may permit direct determination of an accurate set of coordinates relative to the patient based on a known position relative to the reference frame, without continued reliance on the initial registration.

The present disclosure encompasses embodiments of the method 500 that comprise more or fewer steps than those described above, and/or one or more steps that are different than the steps described above.

Figure 6:
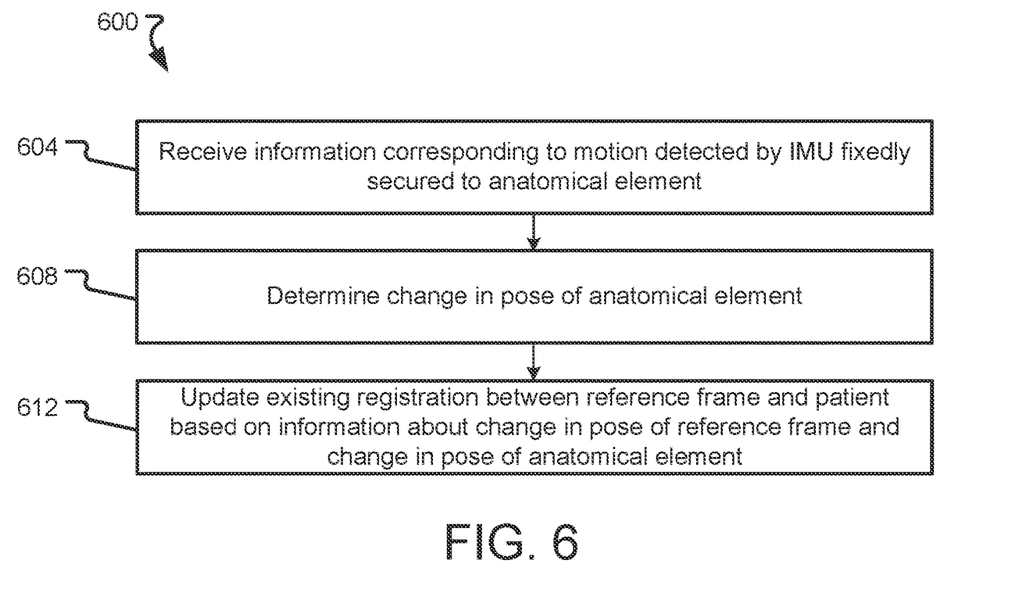
FIG. 6 is a flowchart according to at least one embodiment of the present disclosure.

FIG. 6 depicts a method 600 that may be used, for example, to update an existing registration intraoperatively. The method 600 may be used alone and/or in combination with any other method (or aspect thereof) described herein. In particular, the method 600 may be used in combination with one or more aspects of the method 500 to permit continuous updating of an existing registration, and/or to enable re-registration when patient movement cannot be prevented (or at least assumed to be unlikely to occur) during adjustment of a pose of the reference frame.

The method 600 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 600. The at least one processor may perform the method 600 by executing instructions stored in a memory such as the memory 106. The instructions may correspond to one or more steps of the method 600 described below. The instructions may cause the processor to execute one or more algorithms, such as an image processing algorithm 120, a pose algorithm 122, a transformation algorithm 124, and/or a registration algorithm 126.

The method 600 comprises receiving information corresponding to motion detected by an IMU fixedly secured to an anatomical element of a patient (step 604). The IMU may be an IMU 146 or any other IMU, and may be secured to directly to the anatomical element (e.g., to a surface thereof), or to a portion of a reference frame mount or other tool that is configured to remain fixed relative to the anatomical element (e.g., due to a mechanical, chemical, or other type of attachment between the reference frame mount and the anatomical element). The information may be received via, for example, one or more communication interfaces such as the communication interfaces 108 and/or 150. Thus, the information may be received wirelessly or via a wired connection. The information may identify a new pose of the anatomical element, and/or may be useful for calculating or otherwise determining a new pose of the anatomical element (based, for example, on known information about a previous pose of the anatomical element, or a pose of the anatomical element when the first user input of the step 504 of the method 500 was received).

The method 600 also comprises determining a change in pose of the anatomical element (step 608). The change in pose may be determined, for example, based on the information received in the step 604 and corresponding to motion detected by the IMU. An algorithm such as the pose algorithm 122 may be used to determine the change in pose. Where the information provides the new pose of the anatomical element without the need for any calculation or other determination thereof, the step 608 may be unnecessary.

The method 600 also comprises updating an existing registration between a reference frame and the patient based on information about the change in pose of the reference frame and based on the change in pose of the anatomical element (step 612). The information about the change in pose of the reference frame may be, for example, information such as that received in the step 508 of the method 500, or information resulting from the determination of the change in pose of the reference frame in the step 516 of the method 500. The updated registration may enable a known position relative to the reference frame to be converted into a known position relative to the patient based on a current position of both the reference frame and the patient.

More specifically, the existing registration provides a mapping or other correlation between, for example, a coordinate space of the reference frame and a coordinate space of the patient. The existing registration enables translation or conversion of one or more coordinates in the reference frame coordinate space to one or more coordinates in the patient coordinate space, and/or vice versa. However, any unaccounted-for movement of the reference frame relative to the patient introduces error into the registration, which error may prevent use of the registration for its intended purpose (e.g., to enable image-based guidance during surgery). By affixing an IMU to the patient and another IMU to the reference frame, any relative movement therebetween can be identified and used to update the existing registration, thus preserving an accurate registration. Moreover, this process may occur continuously throughout a surgical procedure, thus avoiding the need for a pause in the surgical procedure to complete a re-registration procedure. Moreover, the method 600 enables accidental bumps or other movements of the reference frame relative to the patient to be detected and accounted for in the registration. And, the method 600 may be completed without exposing the patient to ionizing radiation, in contrast to at least some existing re-registration procedures.

Although the method 600 is directed to detecting relative movement between a reference frame and a patient using IMUs attached to each, other embodiments of the present disclosure may utilize one or more other technologies (including, for example, feature detection, segmentation, or the like) to detect such relative movement.

The present disclosure encompasses embodiments of the method 600 that comprise more or fewer steps than those described above, and/or one or more steps that are different than the steps described above.

As noted above, the present disclosure encompasses methods with fewer than all of the steps identified in FIGS. 2, 3, 4, 5, and 6 (and the corresponding description of the methods 200, 300, 400, 500, and 600), as well as methods that include additional steps beyond those identified in FIGS. 2, 3, 4, 5, and 6 (and the corresponding description of the methods 200, 300, 400, 500, and 600). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A re-registration method comprising:
receiving a first image depicting a reference frame attached to a patient and oriented in a first pose relative to the patient, the first image obtained by an imaging device mounted to a movable support that has been locked in a selected pose;
receiving first input indicating that the reference frame will be adjusted from the first pose relative to the patient to a second pose relative to the patient;
receiving second input indicating that adjustment of the reference frame from the first pose to the second pose is complete;
receiving, subsequent receiving to the second input, a second image depicting the reference frame oriented in the second pose relative to the patient, the second image obtained by the imaging device with the movable support locked in the selected pose; and
updating a registration between the reference frame and the patient to reflect that the reference frame has been moved from the first pose to the second pose.

2. The method of claim 1, comprising:
receiving an initial registration between the reference frame and the patient, the initial registration based on the reference frame being in the first pose relative to the patient.

3. The method of claim 1, wherein the reference frame is attached to the patient via an adjustable reference frame mount.

4. The method of claim 3, wherein when the reference frame is in the first pose, the adjustable reference frame mount is secured to a vertebra of the patient.

5. The method of claim 4, wherein when the reference frame is in the second pose, the adjustable reference frame mount is still secured to the vertebra of the patient.

6. The method of claim 3, wherein the first pose and the second pose are part of a limited number of possible poses of the reference frame relative to the adjustable reference frame mount.

7. The method of claim 6, further comprising:
storing, in memory, information about the limited number of possible poses of the reference frame relative to the adjustable reference frame mount, wherein updating the registration between the reference frame and the patient comprises accessing the stored information.

8. The method of claim 1, wherein the movable support is a robotic arm.

9. The method of claim 1, wherein the movable support comprises at least one selectively lockable joint.

10. The method of claim 1, wherein the second image is obtained by the imaging device within thirty seconds of the reference frame reaching the second pose.

11. The method of claim 1, wherein the imaging device is a navigation system camera.

12. The method of claim 1, wherein the imaging device is a structured light camera.

13. The method of claim 1, wherein the step of updating the registration comprises calculating a transformation between a new reference frame coordinate space and a patient coordinate space based on a previous registration.

14. The method of claim 1, wherein the first input and the second input are based on user input to a user interface.

15. A system for intraoperative re-registration, comprising:
a robotic arm;
an imaging device mounted to the robotic arm;
a processor; and
a memory storing instructions for execution by the processor that, when executed, cause the processor to:
cause the imaging device to capture a first image at a first time, the first image depicting a reference frame attached to a patient and oriented in a first pose relative to the patient;
receive first input indicating that the reference frame will be adjusted from the first pose relative to the patient to a second pose relative to the patient;
receive second input indicating that adjustment of the reference frame from the first pose to the second pose is complete;
cause, subsequent to receiving the second input, the imaging device to capture a second image at a second time after the first time, the second image depicting the reference frame attached to the patient and oriented in the second pose relative to the patient; and
update a registration between the reference frame and the patient to reflect that the reference frame has been moved from the first pose to the second pose.

16. The system of claim 15, wherein the memory stores additional instructions for execution by the processor that, when executed, further cause the processor to:
transmit a signal, before the first time and based on a user input, that causes the robotic arm to be locked in a selected pose.

17. The system of claim 16, wherein the selected pose is a predetermined pose different than a pose of the robotic arm when the signal is transmitted.

18. The system of claim 15, wherein the memory stores additional instructions for execution by the processor that, when executed, further cause the processor to:
determine a first imaging device pose at the first time;
determine a second imaging device pose at the second time; and
determine, based on the first image, the first imaging device pose, the second image, and the second imaging device pose, a transformation between the second pose and the first pose.

19. The system of claim 18, wherein the memory stores additional instructions for execution by the processor that, when executed, further cause the processor to:
update the registration between the reference frame and the patient, based on the determined transformation, to reflect that the reference frame has been moved from the first pose to the second pose.

20. The system of claim 15, wherein causing the imaging device to capture the first image occurs in response to a user input.

* * * * *